(12) United States Patent
Andersson et al.

(10) Patent No.: US 6,257,232 B1
(45) Date of Patent: Jul. 10, 2001

(54) INHALATION DEVICE

(75) Inventors: Jan Andersson, Södra Sandby; Allan Dagsland, Karlshamn; Kjell Wetterlin, Södra Sandby, all of (SE)

(73) Assignee: Astra Akteibolag, Sodertalje (SE)

( * ) Notice: Subject to any disclaimer, the term of this patent is extended or adjusted under 35 U.S.C. 154(b) by 0 days.

(21) Appl. No.: 09/068,474

(22) PCT Filed: Mar. 13, 1998

(86) PCT No.: PCT/SE98/00465

§ 371 Date: May 8, 1998

§ 102(e) Date: May 8, 1998

(87) PCT Pub. No.: WO95/24234

PCT Pub. Date: Sep. 14, 1995

(30) Foreign Application Priority Data

Mar. 14, 1997 (SE) .................................................. 9700937

(51) Int. Cl.⁷ .................................................. A61M 15/00
(52) U.S. Cl. .................................. 128/203.15; 128/203.21
(58) Field of Search ..................... 128/200.23, 203.15, 128/203.12, 203.21, 200.17, 200.18; 604/58; 239/338, 500, 502

(56) References Cited

U.S. PATENT DOCUMENTS

| | | | |
|---|---|---|---|
| 2,470,296 | 5/1949 | Fields | 128/266 |
| 2,573,918 | 11/1951 | McCuiston | 128/206 |
| 3,858,583 | 1/1975 | Hallworth et al. | |
| 3,948,264 | 4/1976 | Wilke et al. | 128/266 |
| 4,524,769 | 6/1985 | Wetterlin | 128/203.15 |
| 4,739,754 | 4/1988 | Shaner | |
| 4,907,583 | * 3/1990 | Wetterlin et al. | 128/203.15 |
| 5,033,463 | * 7/1991 | Cocozza | 128/203.15 |
| 5,372,128 | 12/1994 | Haber et al. | 128/203.21 |
| 5,437,271 | 8/1995 | Hodson et al. | 128/203.15 |
| 5,522,383 | 6/1996 | Calvert et al. | 128/203.15 |
| 5,577,497 | * 11/1996 | Mecikalski et al. | 128/203.15 |

FOREIGN PATENT DOCUMENTS

| | | | |
|---|---|---|---|
| 0069715 | 6/1982 | (EP) | . |
| 0 215 559 A1 | 7/1986 | (EP) | . |
| 0237507 | 2/1987 | (EP) | . |
| 0 705 614 A1 | 4/1990 | (EP) | . |
| 0 640 354 A1 | 9/1991 | (EP) | . |
| 0 573 128 A2 | 11/1991 | (EP) | . |
| 0 520 440 A1 | 6/1992 | (EP) | . |
| 0 703 159 A1 | 9/1995 | (EP) | . |
| 1 295 081 | 11/1972 | (GB) | . |
| 1565029 | 11/1977 | (GB) | 83/14 |
| WO 92/04066 A1 | 3/1992 | (WO) | . |
| WO 92/04068 A1 | 3/1992 | (WO) | . |
| WO 94/11044 A2 | 5/1994 | (WO) | . |
| WO 94/13348 | 6/1994 | (WO) | . |
| WO 94/14492 | 7/1994 | (WO) | . |
| WO 95/24234 | 9/1995 | (WO) | . |

* cited by examiner

Primary Examiner—Aaron J. Lewis
Assistant Examiner—Teena Mitchell
(74) Attorney, Agent, or Firm—Fish & Richardson P.C.

(57) ABSTRACT

An inhaler for administering powder by inhalation, including a plurality of surfaces defining a flow path through which a stream of air is in use drawn on inhalation by a user. The flow path including a mouthpiece; and dosing means for providing a dose of powder to the flow path for entrainment in the stream of air. The inhaler further comprises a movable member downstream of the dosing means for inhibiting accumulation of powder on a surface of the flow path downstream of the dosing means.

39 Claims, 8 Drawing Sheets

INHALATION DEVICE

BACKGROUND

The present invention relates to a powder inhaler for administering powder by inhalation.

A number of powder inhalers are known which use different systems for introducing a dose of powder into an air stream. Typically, the powder is inhaled into the lungs of a patient in order to treat, for example, asthma.

One such powder inhaler is disclosed in EP-A-0237507. This inhaler comprises an inhalation channel and a mouthpiece comprising an air chamber and an outlet nozzle, which together define a flow path through which a stream of air is drawn during inhalation by a user. This inhaler further comprises means for introducing powder into the inhalation channel. During inhalation, air is first drawn into and through the inhalation channel so as to pick up powder. The stream of air containing powder is then drawn through the air chamber and out of the outlet nozzle of the mouthpiece.

Figure 1:
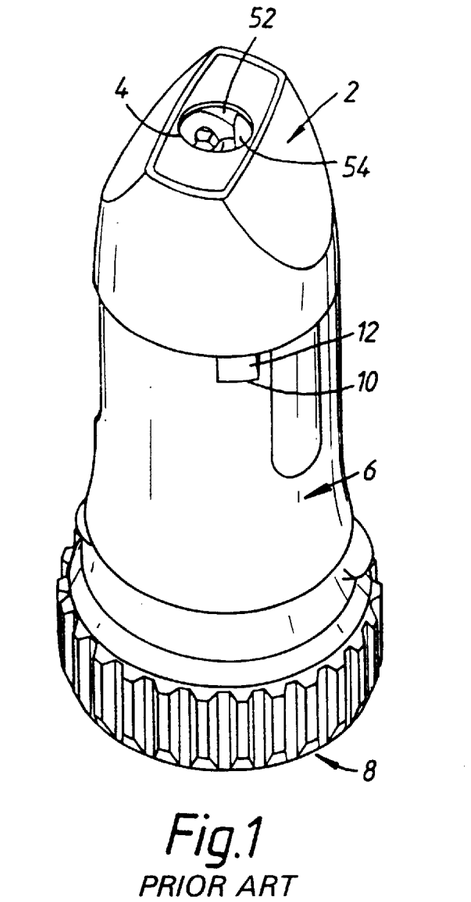
FIG. 1 illustrates a perspective view of a known powder inhaler.

FIG. 1 illustrates such a powder inhaler. The inhaler comprises a mouthpiece 2 comprising an outlet nozzle 4, an inhaler body 6 and a rotatable grip portion 8 for operating a dosing mechanism for providing doses of powder for inhalation. The inhaler body 6 is provided with an opening 10 which is filled with a window 12 through which an indicating wheel 42 is visible so as to provide an indication as to the usage of the inhaler.

Figure 2:
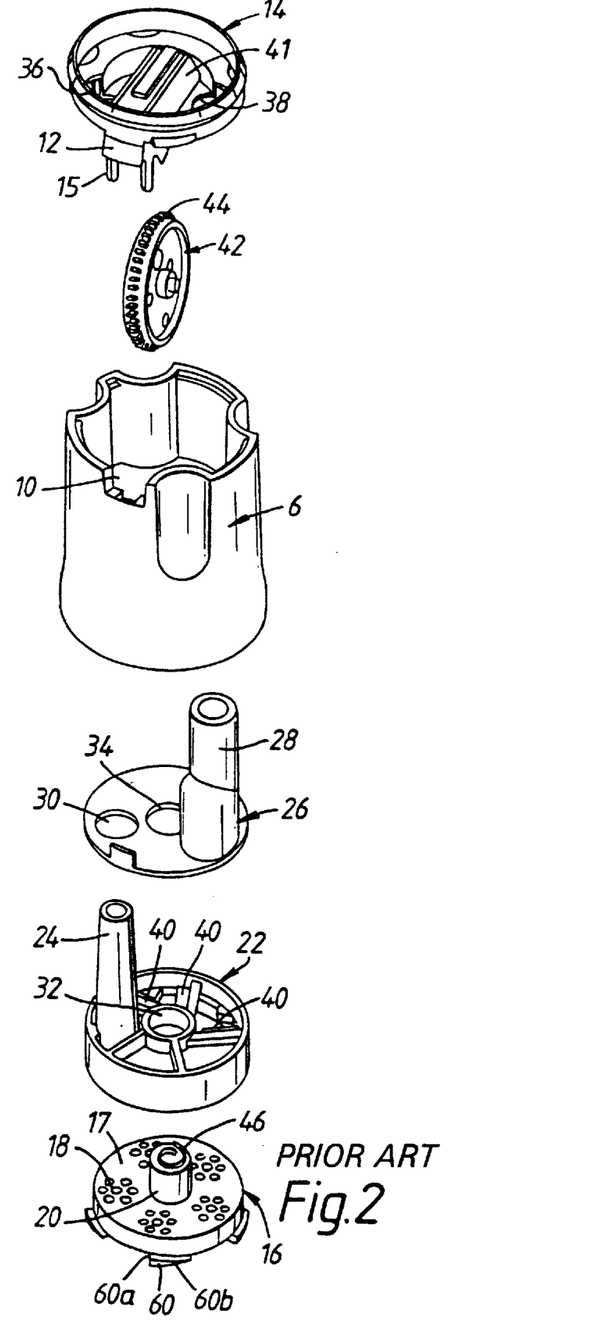
FIG. 2 illustrates in exploded view component parts of the inhaler of FIG. 1.
Figure 3:
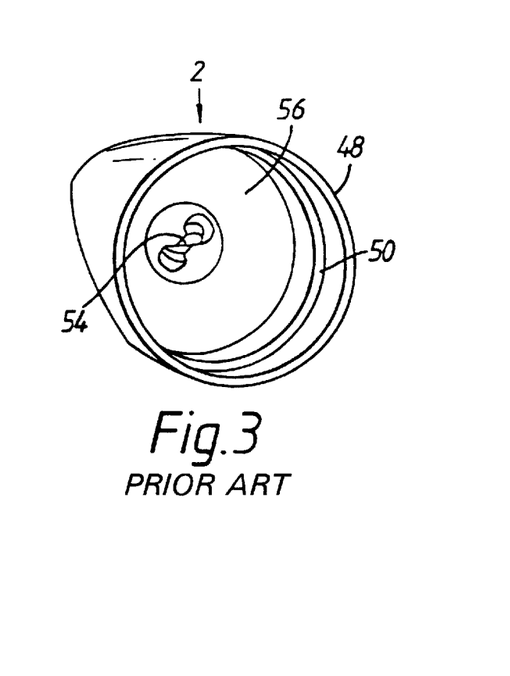
FIG. 3 illustrates the underside of the mouthpiece of the inhaler of FIG. 1.

FIG. 2 illustrates in exploded view component parts disposed within and to the inhaler body 6. The inhaler body 6 is capped with a divider 14 which is fixed thereto. For aesthetic reasons the inhaler body 6 is an opaque moulding. The divider 14 is a transparent moulding which has a depending tongue 15, a part of which forms the window 12.

Within the inhaler body 6 are housed the component parts of the dosing mechanism. These component parts include a dosing unit 16 which comprises a member 17 having a planar surface in which a plurality of dosing means 18 are provided and a shaft 20 which extends axially from the centre of the member 17, an inhalation unit 22 which comprises an inhalation channel 24 and a storage unit 26 which comprises a storage chamber 28 for storing powder. The above-mentioned component parts of the dosing mechanism are assembled by passing the inhalation channel 24 through an opening 30 in the storage unit 26 and passing the shaft 20 through central openings 32, 34 in the inhalation unit 22 and the storage unit 26 respectively. When so assembled, the upper ends of the inhalation channel 24 and the storage chamber 28 pass respectively through first and second openings 36, 38 in the divider 14. In this way, the inhalation unit 22 and the storage unit 26 are fixed in position in relation to one another and the dosing unit 16 can be rotated relative thereto.

In this inhaler the storage unit 28 is open at the bottom such that in use powder is provided to the dosing unit 16 under the action of gravity and the inhalation unit 22 further comprises scrapers 40 which are resiliently biased against the surface of the member 17 in which the dosing means 18 are provided. In this way, as the dosing unit 16 is rotated, the dosing means 18, which in this inhaler comprise a plurality of through holes, are filled with powder by the scrapers 40. Powder is prevented from passing through the dosing means 18 by a plate (not illustrated) which is disposed beneath the dosing unit 16.

As illustrated in FIG. 2, the divider 14 further comprises supporting means 41 for rotatably supporting an indicating wheel 42. The indicating wheel 42 has a plurality of teeth 44 disposed around the periphery thereof which engage with a spiral groove or protrusion 46 on the end face of the shaft 20. The supporting means 41 is configured to align the indicating wheel 42 such that a part of the periphery thereof is disposed adjacent the inner surface of the window 12. In use, as the dosing unit 16 is rotated, the spiral groove or protrusion 46 engages with one or more of the teeth 44 on the indicating wheel 42 so as to rotate the same. In this way, by providing a coloured marking on the periphery of the indicating wheel 42, it is possible to provide the user with a visible indication at the window 12 as to the usage of the inhaler.

Figure 4:
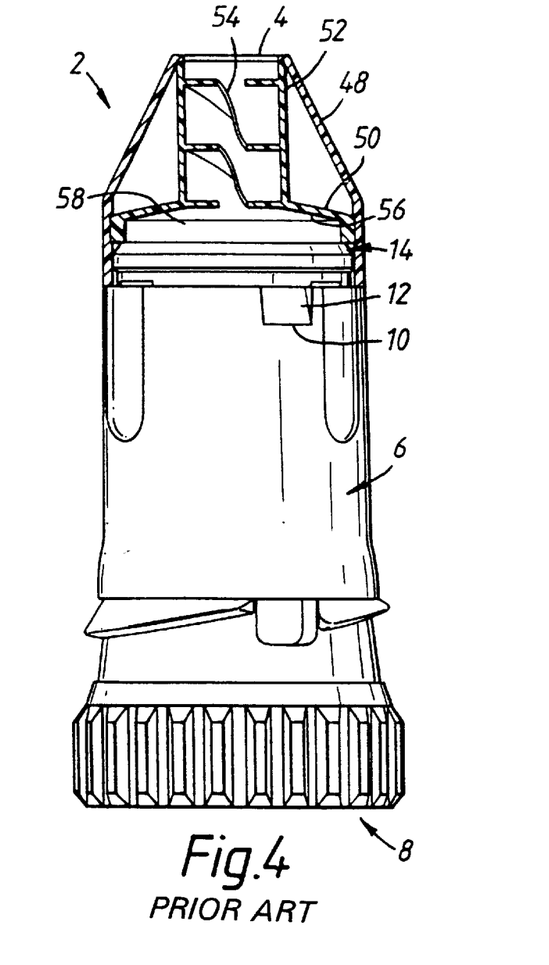
FIG. 4 illustrates a part-sectional side view of the inhaler of FIG. 1.

As illustrated in FIG. 4, the mouthpiece 2 is fixed to the divider 14. The mouthpiece 2 comprises first and second parts 48, 50, the first part 48 being the part which is gripped by the lips of a user and the second part 50 being an insert fitted within the first part 48. The second part or insert 50 comprises a tubular section 52, which includes one or more spirally or helically shaped projections 54 that act to deflect the air drawn therethrough and thereby deagglomerate any larger particles of entrained powder, and a substantially radially-directed flange 56, which provides a surface that together with upper surface of the divider 14 defines an air chamber 58 that is in fluid communication with the inhalation channel 24 through which air containing powder is drawn on inhalation by a user.

In use, as described hereinabove, powder is transferred from the storage chamber 28 to one of the dosing means 18, and, with rotation of the dosing unit 16, the one dosing means 18 provides a dose of powder to the inhalation channel 24. In this inhaler the dosing unit 16 is rotated by rotating the grip portion 8 in one sense, the counter-clockwise sense when viewed from above, between first and second angularly-spaced positions. For this purpose the dosing unit 16 comprises wedge-shaped elements 60 disposed around the periphery of the member 17 and the grip portion 8 comprises a resilient member (not illustrated) which is configured to engage with an axially-directed surface 60a of a respective one of the wedge-shaped elements 60 so as to rotate the dosing unit 16 by pushing the respective wedge-shaped element 60. On rotation of the grip portion 8 in the opposite sense, the clockwise sense when viewed from above, between the second and the first angularly-spaced positions, the dosing unit 16 remains stationary and the resilient member is located behind the axially-directed surface 60a of the adjacent wedge-shaped element 60; the resilient member riding over an inclined surface 60b of the adjacent wedge-shaped element 60.

Although the above-described known powder inhaler functions quite adequately, powder may possibly accumulate on surfaces in the flow path therethrough.

U.S. Pat. No. 4524769 discloses a powder inhaler in which the mouthpiece includes rotating means provided for deagglomerating powder agglomerates drawn therethrough. The deagglomeration of powder agglomerates is facilitated by air inlets disposed around the periphery of the mouthpiece. None of these inhalers, however, address the problem of powder accumulation on surfaces in the flow path therethrough as identified hereinabove.

It is thus an aim of the present invention to provide a powder inhaler having a construction which is such as to reduce the possibility of powder accumulating on surfaces in the flow path therethrough.

SUMMARY OF THE INVENTION

In one aspect, the present invention provides an inhaler for administering powder by inhalation, comprising: a flow path defined by a plurality of surfaces through which a stream of air is in use drawn on inhalation by a user, the flow path including a mouthpiece; and dosing means for providing a dose of powder to the flow path for entrainment in the stream of air; characterized in that the inhaler further comprises a movable member downstream of the dosing means for inhibiting accumulation of powder on a surface of the flow path downstream of the dosing means.

Embodiments of this aspect of the invention may include one or more of the following features.

Preferably, the flow path includes a chamber having an inlet and an outlet.

More preferably, the movable member interrupts the stream of air drawn through the inlet of the chamber and is movable at least partially by the stream of air.

Still more preferably, the movable member is a rotatable member which is rotatable about an axis within the chamber and is disposed opposite the inlet of the chamber so as, in use, to present a moving surface towards which the stream of air containing powder drawn through the inlet of the chamber is directed.

Yet more preferably, the rotatable member includes at least one element on which the stream of air drawn through the inlet of the chamber acts so as to cause rotation of the rotatable member on inhalation by the user.

In one embodiment the rotatable member comprises a disc comprising a plurality of angled arms.

Preferably, the angled arms are shaped and configured so as to provide no direct flow path between the inlet and the outlet of the chamber.

In another embodiment the rotatable member comprises a tubular section having disposed therein at least one spirally or helically shaped projection and a radially outwardly-extending flange which defines a surface of the chamber.

Preferably, the flange is disposed opposite the inlet of the chamber.

More preferably, a surface of the flange opposed to the inlet of the chamber includes a relief profiling.

In one embodiment the relief profiling comprises an array of recesses.

In another embodiment the relief profiling comprises an array of projections.

Preferably, the mouthpiece comprises a first, outer part which is gripped by the lips of the user and a second, inner part disposed therewithin, the rotatable member comprising the inner part, with the lower surface of the flange defining an upper surface of the chamber.

Preferably, a circumferential outer surface of the flange is a close sliding fit with a circumferential inner surface of the outer part of the mouthpiece.

More preferably, the flange includes a downwardly-depending peripheral skirt which defines the circumferential outer surface of the flange.

In one embodiment the outer part of the mouthpiece includes a central spindle about which the inner part of the mouthpiece is rotatably mounted.

In another embodiment the outer part of the mouthpiece includes an annular sleeve within which the inner part of the mouthpiece is rotatably mounted.

Preferably, the outer part of the mouthpiece includes a plurality of holes disposed in spaced relation about the periphery thereof through which supplementary air is drawn on inhalation by the user and the inner part of the mouthpiece includes at least one air deflecting member which is adapted so as to be acted upon by the supplementary air drawn through the plurality of holes.

In one embodiment the at least one air deflecting member comprises a plurality of flutes provided to the circumferential outer surface of the inner part of the mouthpiece and the plurality of holes in the outer part of the mouthpiece are disposed in opposed relation to the circumferential outer surface of the inner part of the mouthpiece.

In one preferred embodiment the flutes are aligned parallel to the axis of rotation of the inner part of the mouthpiece.

In another preferred embodiment the flutes are inclined to the axis of rotation of the inner part of the mouthpiece.

In another embodiment the at least one air deflecting member comprises a plurality of angled blades surrounding the tubular section of the inner part of the mouthpiece.

In an alternative embodiment the mouthpiece comprises a tubular section having disposed therein at least one spirally or helically shaped projection and a radially outwardly-extending flange which defines a surface of the chamber, and the rotatable member is rotatably mounted adjacent a surface of the flange defining the surface of the chamber.

Preferably, the lower surface of the flange defines an upper surface of the chamber.

More preferably, the flange is disposed opposite the inlet of the chamber.

In one embodiment the rotatable member comprises a disc.

Preferably, the disc has the form of a downwardly-opening cone.

Preferably, the disc includes at least one substantially centrally located hole.

Preferably, a circumferential outer surface of the disc is a close sliding fit with a circumferential inner surface of the chamber.

More preferably, the disc includes a downwardly-depending peripheral skirt which defines the circumferential outer surface thereof.

Preferably, the chamber includes a plurality of holes disposed in spaced relation about the periphery thereof through which supplementary air is in use drawn on inhalation by the user and the disc includes at least one air deflecting member which is adapted so as to be acted upon by the supplementary air drawn through the plurality of holes.

In one embodiment the at least one air deflecting member comprises a plurality of flutes provided to the circumferential outer surface of the disc and the plurality of holes are disposed in opposed relation to the circumferential outer surface of the disc.

In one preferred embodiment the flutes are aligned parallel to the axis of rotation of the disc.

In another preferred embodiment the flutes are inclined to the axis of rotation of the disc.

In another embodiment the at least one air deflecting member comprises a plurality of fins disposed on a surface of the disc directed away from the inlet of the chamber.

Preferably, the fins are substantially radially directed.

Preferably, a surface of the disc opposed to the inlet of the chamber includes a relief profiling.

In one embodiment the relief profiling comprises an array of recesses.

In another embodiment the relief profiling comprises an array of projections.

The powder inhaler of the present invention may be used with any suitable form of powder, including powders introduced into the air stream in the raw state or as conglomerate, micronized or ordered mixture particles. Furthermore, the active ingredient or ingredients of the powder may be diluted with one or more substances such as lactose and may be for the treatment of various conditions, not necessarily respiratory conditions. Indeed, the powder can include genetic material and need not be restricted to human use only.

Medicaments suitable for administration by the powder inhaler of the present invention are any which may be delivered by inhalation and include for example β2-adrenoreceptor agonists, for example, salbutamol, terbutaline, rimiterol, fenoterol, reproterol, adrenaline, pirbuterol, isoprenaline, orciprenaline, bitolterol, salmeterol, formoterol, clenbuterol, procaterol, broxaterol, picumeterol, TA-2005, mabuterol and the like, and their pharmacologically acceptable esters and salts; anticholinergic bronchodilators, for example, ipratropium bromide and the like; glucocorticosteroids, for example, beclomethasone, fluticasone, budesonide, tipredane, dexamethasone, betamethasone, fluocinolone, triamcinolone acetonide, mometasone and the like, and their pharmacologically acceptable esters and salts; antiallergic medicaments, for example, sodium cromoglycate and nedocromil sodium; expectorants; mucolytics; antihistamines; cyclooxygenase inhibitors; leukotriene synthesis inhibitors; leukotriene antagonists; phospholipase-A2 (PLA2) inhibitors; platelet aggregating factor (PAF) antagonists and prophylactics of asthma; antiarrhythmic medicaments; tranquilisers; cardiac glycosides; hormones; antihypertensive medicaments; antidiabetic medicaments; antiparasitic medicaments; anti-cancer medicaments; sedatives; analgesic medicaments; antibiotics; antirheumatic medicaments; immunotherapies; antifungal medicaments; antihypotension medicaments; vaccines; antiviral medicaments; proteins; polypeptides and peptides, for example, peptide hormones and growth factors; polypeptide vaccines; enzymes; endorphines; lipoproteins and polypeptides involved in the blood coagulation cascade; vitamins; and others, for example, cell surface receptor blockers, antioxidants, free radical scavengers and organic salts of N,N'-diacetylcystine.

Preferred embodiments of the present invention will now be described hereinbelow by way of example only with reference to the accompanying drawings.

DETAILED DESCRIPTION OF THE PREFERRED EMBODIMENT

Structurally, the powder inhalers in accordance with the preferred embodiments of the present invention have many features in common with the above-described known powder inhaler. For this reason, and in order to avoid unnecessary duplication of description, only the structural differences will be described in detail and reference is made to the preceding description of the known powder inhaler.

Figure 5:
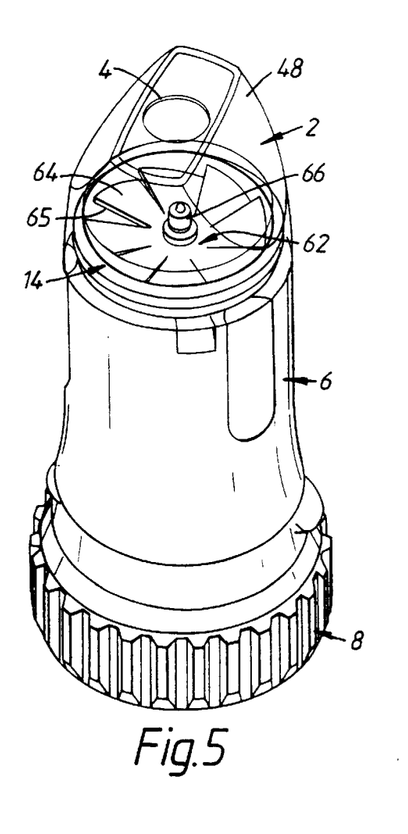
FIG. 5 illustrates a perspective view of a powder inhaler in accordance with a first embodiment of the present invention.
Figure 6:
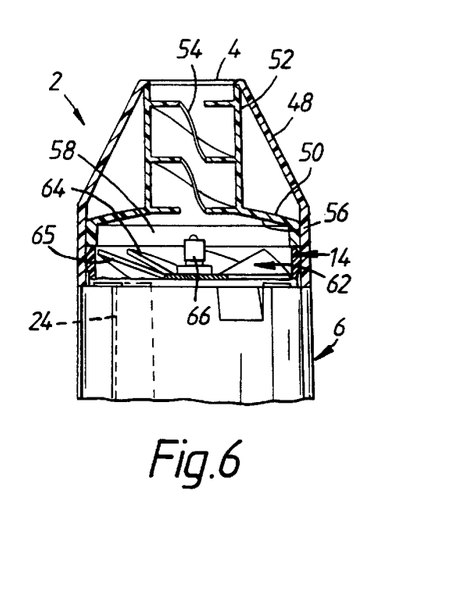
FIG. 6 illustrates a fragmentary part-sectional side view of the inhaler of FIG. 5.

FIGS. 5 and 6 illustrate a powder inhaler in accordance with a first embodiment of the present invention.

This inhaler is a modification of the above-described known powder inhaler. As in the above-described known powder inhaler, this inhaler comprises a mouthpiece 2, an inhaler body 6 and a rotatable grip portion 8. In FIG. 5, for convenience of illustration, the mouthpiece 2 is illustrated in phantom with the second part or insert 50 thereof (corresponding to the insert 50 of the mouthpiece 2 of the above-described known powder inhaler) omitted in order that the features of the inhaler ordinarily concealed thereby may be clearly illustrated. This inhaler differs from the above-described known powder inhaler in further comprising a rotatable member, in this embodiment a rotatable disc 62, having, similarly to a fan, a plurality of angled arms 64 which define an undersurface 65 which opposes the outlet of the inhalation channel 24 (illustrated in phantom in FIG. 6) through which a stream of air containing powder is in use drawn on inhalation by a user. The disc 62 is disposed in the air chamber 58 so as to rotate in a plane parallel to the upper surface of the divider 14 which has associated therewith the outlet of the inhalation channel 24. The angled arms 64 of the disc 62 are shaped and configured so that there is no direct, that is uninterrupted, flow path therethrough from the inhalation channel 24 to the opposing surface of the air chamber 58 defined by the lower surface of the flange 56 of the insert 50. In this embodiment the disc 62 is fitted to the divider 14 by an axial fitting 66.

In use, when a user inhales by sucking through the mouthpiece 2, a stream of air containing powder is drawn through the inhalation channel 24. This stream of air impacts upon the disc 62 causing the same to rotate. Since the disc 62 interrupts the stream of air drawn through the inhalation channel 24, preferably by forming an indirect flow path as described hereinabove, powder drawn through the air chamber 58 past the angled arms 64 of the disc 62 is prevented from accumulating on the lower surface of the flange 56 of the insert 50 opposite the outlet of the inhalation channel 24. Instead, any powder which accumulates deposits continuously around the undersurface 65 of the disc 62 as a thin film. Furthermore, powder is prevented from accumulating on the undersurface 65 of the disc 62 in any appreciable amount as any powder which accumulates is tended to be flung from the undersurface 65 by the centrifugal force developed on rotation of the disc 62. In this way, powder is prevented from depositing on surfaces within the flow path or is at least continuously dislodged so as to prevent any appreciable accumulation thereon.

FIGS. 7 and 8 illustrate a powder inhaler in accordance with a second embodiment of the present invention, with a first modification being illustrated in FIGS. 9 and 10 and a second modification being illustrated in FIG. 11.

This inhaler is a modification of the above-described known powder inhaler. As in the above-described known powder inhaler, this inhaler comprises a mouthpiece 2, an inhaler body 6 and a rotatable grip portion 8 (not illustrated). This inhaler differs from the above-described known powder inhaler in that the second part or insert 70 of the mouthpiece 2 is rotatably mounted about a spindle 72 which depends downwardly from a crossbeam member 74 that is fixed across and just beneath the outlet nozzle 4 of the outer, first part 48 of the mouthpiece 2. The spindle 72 is located in a tubular member 76 which has a closed lower end 78 and is centrally axially mounted within the tubular section 79 of the inset 70, whereby the spirally or helically shaped projections 81 of the tubular section 79 surround the tubular member 76. The flange 83 of the insert 70 includes a downwardly-depending annular skirt 80 having a circumferential outer surface 82 which is a close, yet freely movable, fit with the corresponding circumferential inner surface 85 of a lower tubular part 84 of the first part 48 of the mouthpiece 2.

In use, when a user inhales by sucking on the mouthpiece 2, a stream of air containing powder is drawn through the inhalation channel 24 (illustrated in phantom in FIG. 7), through the air chamber 58 and upwardly through the tubular section 79 around the spirally or helically shaped projections 81. The flow of the stream of air past the spirally or helically shaped projections 81 imparts a rotational moment to the insert 70 about the spindle 72. This rotational moment causes a constantly moving annular part of the undersurface 86 of the flange 83 to be disposed above the outlet of the inhalation channel 24. The provision of this constantly moving surface towards which the stream of air containing powder is directed tends to prevent localized accumulation of powder, which could happen if the insert 70 were stationary, as a result of a large surface area being presented in a continuously moving fashion above the inhalation channel 24 and the flow being turbulent being at that surface. In addition, any powder which deposits on that moving surface tends to be prevented from accumulating in any appreciable amount as a result of the centrifugal forces developed on rotation of the insert 70 which tend to break up any large bodies of powder that may form. In this way, the possibility of large bodies of powder being formed in the flow path of the inhaler is significantly reduced, thereby preventing a user from receiving an unusually large dose of powder during any given inhalation.

FIGS. 9 and 10 illustrate a first modification of the insert 70 of the inhaler of the above-described second embodiment. In this modification the undersurface 86 of the flange 83 is provided with a relief profiling 92 in the form of an array of small recesses 94. By way of example, the recesses 94 can be any of part-spherical, typically hemi-spherical, or frusto-spherical, the latter consisting of a part-spherical innermost portion inwardly of a frusto-conical portion. The array of recesses 94 is illustrated in FIG. 10. It will be seen that the recesses 94 are closely packed.

FIG. 11 illustrates a second modification of the insert 70 of the inhaler of the above-described second embodiment. In this modification the undersurface 86 of the flange 83 is provided with a relief profiling 92 in the form of an array of small projections 96. Again, by way of example, the projections 96 can be any of part-spherical, typically hemi-spherical, or frusto-spherical, the latter consisting of a frusto-spherical innermost portion inwardly of a part-spherical portion. Preferably, the array of projections 96 has the same packing as the recesses 94 illustrated in FIG. 10.

In both of the above-described modifications, the provision of recesses 94 and projections 96 on the undersurface 86 of the flange 83 assists in preventing the accumulation of powder which impacts thereagainst as a result of the stream of air containing powder being sucked upwardly through the inhalation channel 24. Specifically, the recesses 94 and the projections 96 provide an enhanced turbulent flow adjacent the undersurface 86 of the flange 83, thereby inhibiting the deposition of powder.

FIGS. 12 to 14 illustrate a powder inhaler in accordance with a third embodiment of the present invention, with a modification being illustrated in FIG. 15.

This inhaler is a modification of the inhaler of the above-described second embodiment and incorporates means for providing an additional rotational force to the insert 70 of the mouthpiece 2. In this embodiment the insert 70 is, inhaler of the above-described second embodiment, rotatably mounted about the spindle 72. However, this inhaler differs from the inhaler of the above-described second embodiment in that the circumferential outer surface 82 of the skirt 80 includes a plurality of substantially axially-directed flutes 102 and in that the lower tubular part 84 of the first part 48 of the mouthpiece 2 includes a plurality of angularly-spaced peripheral holes 104 extending circumferentially therearound which are located so as to coincide with the circumferential outer surface 82 of the insert 70. In this embodiment the holes 104 are rectangular and elongate in the circumferential direction. In practice, however, the holes 104 may be of any shape and configuration. For example, the holes 104 could be circular. In one preferred embodiment the mouthpiece 2 includes four uniformly-spaced holes 104. The provision of the holes 104 in the lower tubular part 84 of the first part 48 of the mouthpiece 2 provides additional openings through which supplementary air is drawn when a user inhales by sucking on the mouthpiece 2.

In use, when a user inhales by sucking on the mouthpiece 2, air is drawn not only through the inhalation channel 24 (illustrated in phantom in FIG. 12) but also inwardly through the holes 104, which supplementary air drawn through the holes 104 is directed against the flutes 102 on the circumferential outer surface 82 of the insert 70. This incoming supplementary air tends to impart an additional rotational force on the insert 70, thereby increasing the rotational effect and further reducing the possibility of powder accumulating on surfaces, particularly the undersurface 86, of the insert 70. In this embodiment, the supplementary air, after impacting on the flutes 102, passes downwardly into the air chamber 58, and thereafter upwardly through the spirally or helically shaped projections 81 in the tubular section 79. In an alternative embodiment the inhaler can be configured such that the supplementary air is deflected upwardly from the flutes 102 and thereafter through the outlet nozzle 4 of the mouthpiece 2 via a gap 105 between the outer surface 106 of the tubular section 79 of the insert 70 and the inner surface 108 of the first part 48 of the mouthpiece 2.

Figure 15:
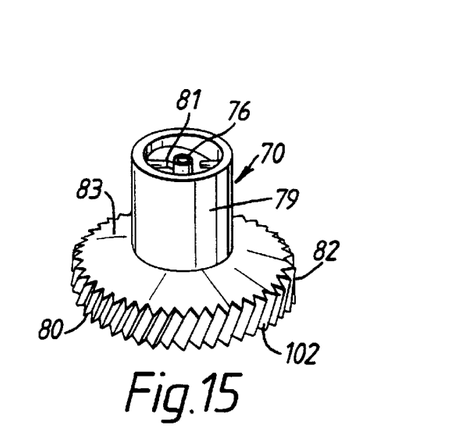
FIG. 15 illustrates a perspective view of a modification of the insert of FIG. 14.

FIG. 15 illustrates a modification to the insert 70 of the inhaler of the above-described third embodiment. In this embodiment the flutes 102 on the circumferential outer surface 82 of the skirt 80 are arranged so as to be inclined at an angle, typically around 45°, relative to the axial direction. The provision of such inclined flutes 102 imparts a yet further additional rotational force to the insert 70 when a user inhales by sucking through the mouthpiece 2.

Figure 16:
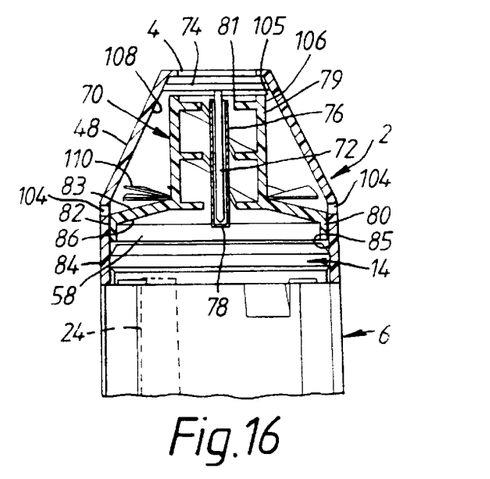
FIG. 16 illustrates a fragmentary part-sectional side view of a powder inhaler in accordance with a fourth embodiment of the present invention.
Figure 17:
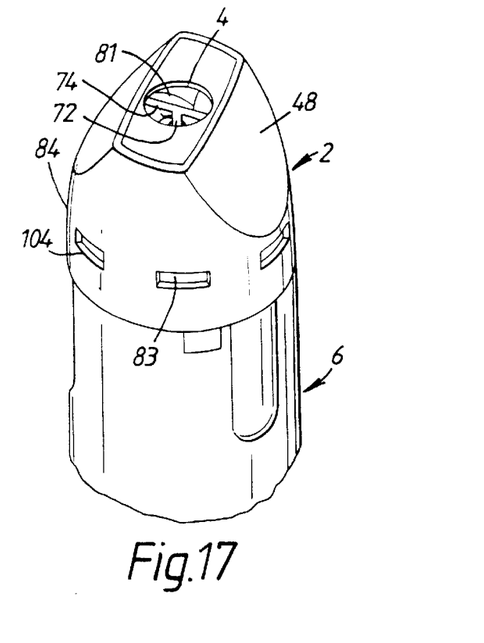
FIG. 17 illustrates a fragmentary perspective view of the inhaler of FIG. 16.
Figure 18:
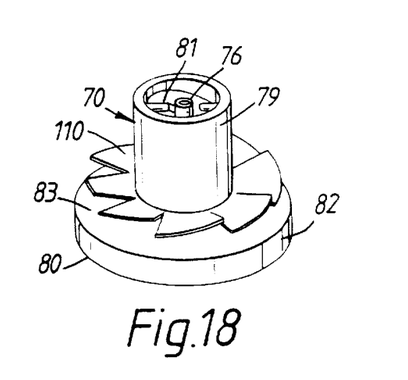
FIG. 18 illustrates a perspective view of the insert of the mouthpiece of the inhaler of FIG. 16.

FIGS. 16 to 18 illustrate a powder inhaler in accordance with a fourth embodiment of the present invention.

This inhaler is a modification of the inhaler of the above-described third embodiment. In this embodiment, similarly to the inhaler of the above-described third embodiment, the insert 70 is rotatably mounted about the spindle 72 and means are provided for imparting an additional rotational force to the insert 70 for reducing the possibility of powder accumulating on the undersurface 86 thereof. This inhaler differs from the inhaler of the above-described third embodiment in that, similarly to the inhaler of the above-described second embodiment, the circumferential outer surface 82 of the skirt 80 of the flange 83 of the insert 70 is smooth and forms a close but sliding fit with the circumferential inner surface 85 of the lower tubular part 84 of the first part 48 of the mouthpiece 2. This inhaler further differs from the inhaler of the above-described third embodiment in that the insert 70 further comprises a plurality of angled arms 110, having the form of the vanes of a fan or turbine wheel, disposed around the lower end of the tubular section 79 of the insert 70 and above the flange 83. Again, similarly to the inhaler of the above-described third embodiment, a plurality of angularly-spaced peripheral holes 104 are disposed around the lower tubular part 84 of the first part 48 of the mouthpiece 2. Differently from the inhaler of the above-described third embodiment, however, the peripheral holes 104 are located at an axial position above the circumferential outer surface 82 of the skirt 80. The provision of the holes 104 in the lower tubular part 84 of the first part 48 of the mouthpiece 2 provides additional openings through which supplementary air is drawn when a user inhales by sucking on the mouthpiece 2.

In use, when a user inhales by sucking on the mouthpiece 2, air is drawn not only through the inhalation channel 24 (illustrated in phantom in FIG. 16) but also inwardly through the peripheral holes 104, where the supplementary air drawn through the holes 104 is directed against the angled arms 110 on the tubular section 79. This incoming supplementary air tends to impart an additional rotational force on the insert 70, thereby increasing the rotational effect and further reducing the possibility of powder accumulating on surfaces, particularly the undersurface 86, of the insert 70. In this embodiment, the supplementary air, after impacting on the angled arms 110, passes upwardly through the outlet nozzle 4 via the gap 105 between the outer surface 106 of the tubular section 79 and the inner surface 108 of the first part 48 of the mouthpiece 2.

Figure 19:
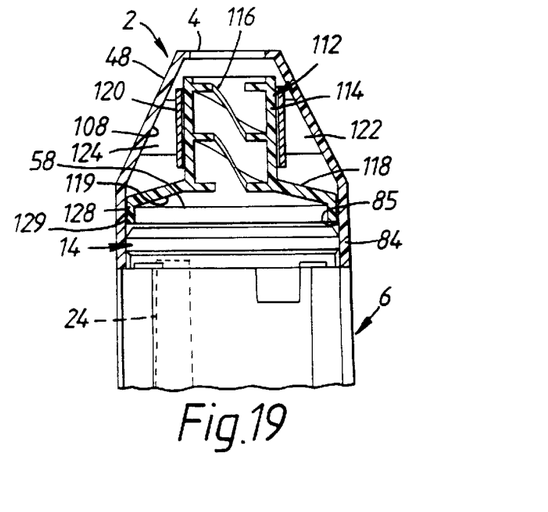
FIG. 19 illustrates a fragmentary part-sectional side view of a powder inhaler in accordance with a fifth embodiment of the present invention.
Figure 20:
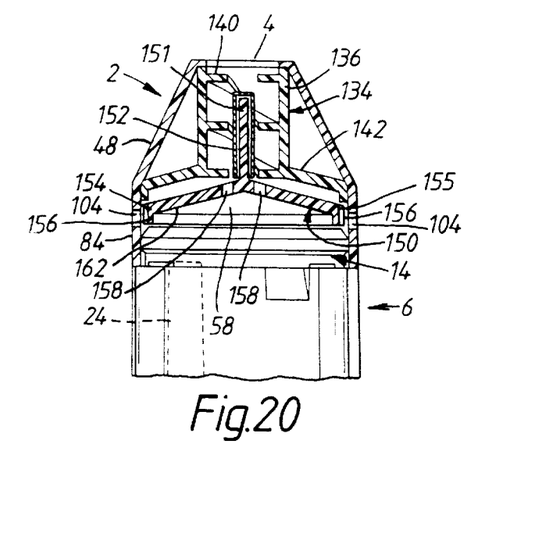
FIG. 20 illustrates a fragmentary part-sectional side view of a powder inhaler in accordance with a sixth embodiment of the present invention.
Figure 21:
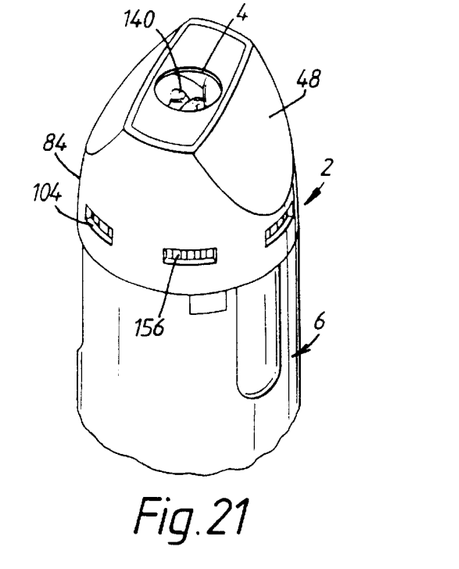
FIG. 21 illustrates a fragmentary perspective view of the inhaler of FIG. 20.
Figure 22:
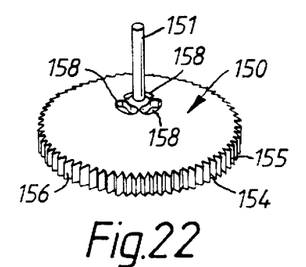
FIG. 22 illustrates a perspective view of the rotatable disc of the inhaler of FIG. 20.
Figure 23:
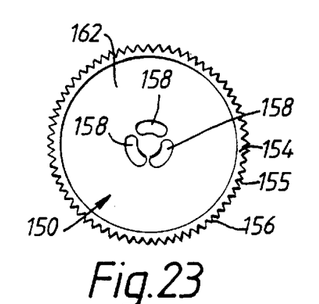
FIG. 23 illustrates a bottom view of the rotatable disc of FIG. 22.

FIG. 19 illustrates a powder inhaler in accordance with a fifth embodiment of the present invention.

Figure 7:
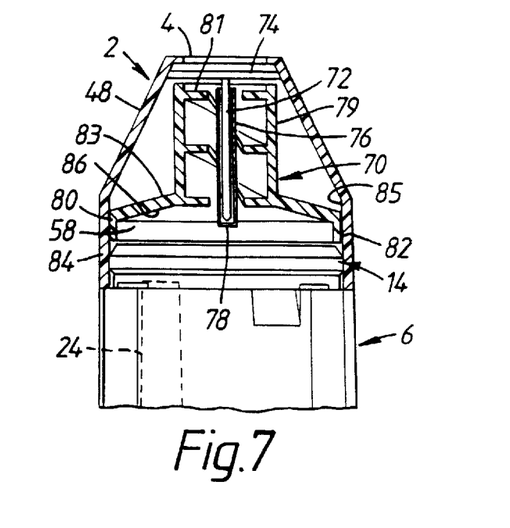
FIG. 7 illustrates a fragmentary part-sectional side view of a powder inhaler in accordance with a second embodiment of the present invention.
Figure 8:
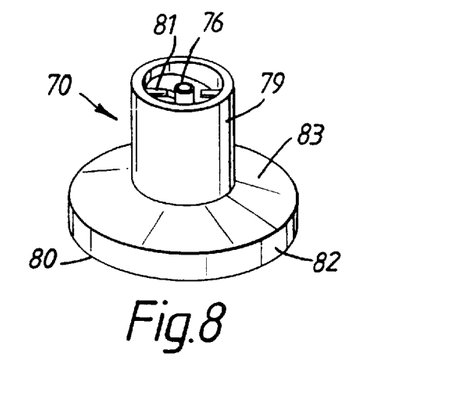
FIG. 8 illustrates a perspective view of the insert of the mouthpiece of the inhaler of FIG. 7.
Figure 12:
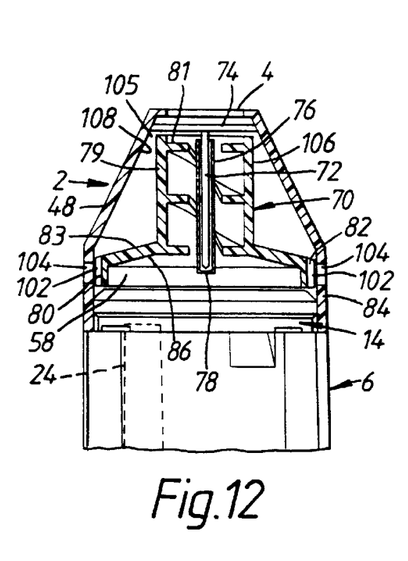
FIG. 12 illustrates a fragmentary part-sectional side view of a powder inhaler in accordance with a third embodiment of the present invention.
Figure 13:
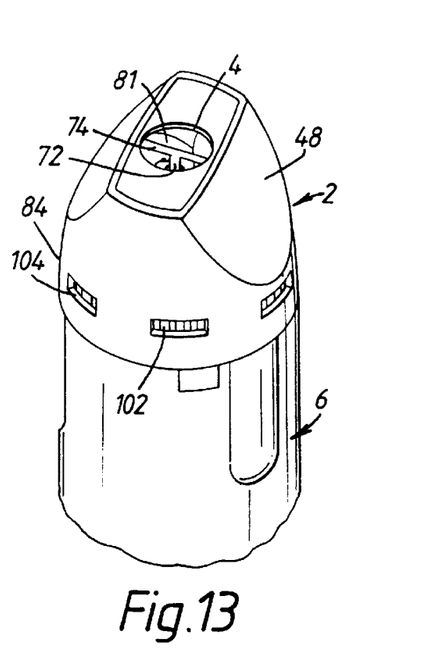
FIG. 13 illustrates a fragmentary perspective view of the inhaler of FIG. 12.
Figure 14:
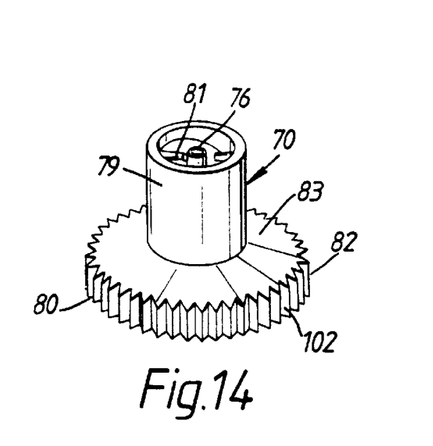
FIG. 14 illustrates a perspective view of the insert of the mouthpiece of the inhaler of FIG. 12.

This inhaler is a modification of the inhaler of the above-described second embodiment. As in the inhaler of the above-described second embodiment, the insert 112 comprises a tubular section 114 which includes one or more spirally or helically shaped projections 116 that act to deflect the air drawn therethrough and thereby deagglomerate any larger particles of entrained powder, and a substantially radially-directed flange 118, which has an undersurface 119 that together with upper surface of the divider 14 defines the air chamber 58 (as depicted in FIGS. 7 and 12). This inhaler differs from the inhaler of the above-described second embodiment in that the insert 112 is rotatably mounted to a tubular sleeve 120 which is fixed by a pair of opposed mounts 122, 124 to the inner surface 108 of the first part 48 of the mouthpiece 2. In this embodiment the cylindrical outer surface of the tubular section 114 and the cylindrical inner surface of the tubular sleeve 120 act as bearing surfaces which allow for free rotation of the tubular section 114 within the tubular sleeve 120. Again, as in the inhaler of the above-described second embodiment, the flange 118 has a downwardly depending skirt 128, the circumferential outer surface 129 of which is arranged to provide a close, yet sliding fit, with the circumferential inner surface 85 of the lower tubular part 84 of the first part 48 of the mouthpiece 2.

In use, when a user inhales by sucking through the mouthpiece 2, a stream of air containing powder is drawn through the inhalation channel 24 (illustrated in phantom), and, as in the inhaler of the above-described second embodiment, the insert 112 is caused to rotate as a result of the flow of that stream of air through the spirally or helically shaped projections 116 in the tubular section 114.

Figure 9:
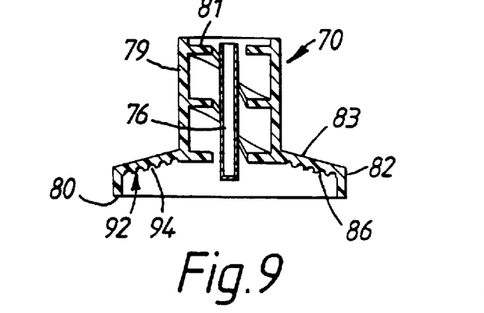
FIG. 9 illustrates a vertical cross-sectional view of a first modification of the insert of FIG. 8.
Figure 10:
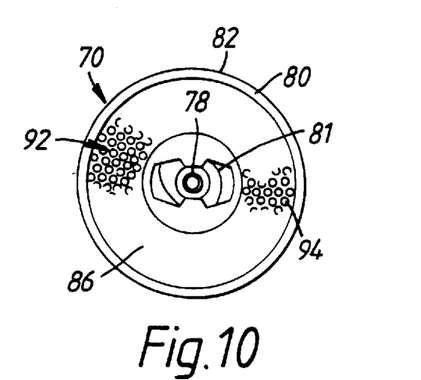
FIG. 10 illustrates a bottom view of the insert of FIG. 9.
Figure 11:
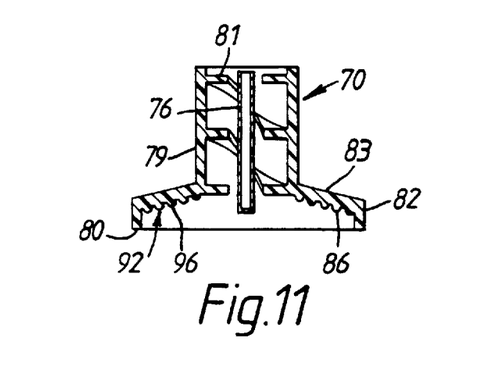
FIG. 11 illustrates a vertical cross-sectional view of a second modification of the insert of FIG. 8.

In each of the inhalers of the above-described third to fifth embodiments, the undersurface 86, 119 of the flange 83, 118 of the insert 70, 112 which faces the inhalation channel 24 may be provided with a relief profiling of the kind as described in relation to FIGS. 9 to 11.

Figure 24:
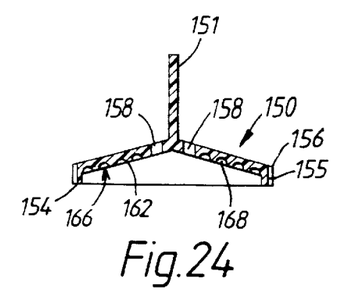
FIG. 24 illustrates a vertical cross-sectional view of a first modification of the rotatable disc of FIG. 22.
Figure 25:
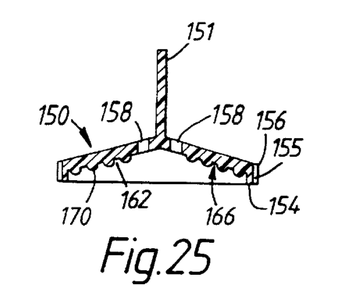
FIG. 25 illustrates a vertical cross-sectional view of a second modification of the rotatable disc of FIG. 22.

FIGS. 20 to 23 illustrate a powder inhaler in accordance with the sixth embodiment of the present invention, with modifications being illustrated in FIGS. 24 and 25.

This inhaler is a modification of the above-described known powder inhaler. As in the above-described known powder inhaler, this inhaler comprises a mouthpiece 2, an inhaler body 6 and a rotatable grip portion 8 (not illustrated). In this embodiment, again as in the above-described known powder inhaler, the first part 48 and the second part or insert 134 of the mouthpiece 2 are fixed to one another. Again, similarly to the above-described known powder inhaler, the insert 134 comprises a tubular section 136 which includes one or more spirally or helically shaped projections 140 that act to deflect the air drawn therethrough and thereby deagglomerate any larger particles of entrained powder, and a substantially radially-directed flange 142, which provides a surface that together with upper surface of the divider 14 defines the air chamber 58. This inhaler differs from the above-described known powder inhaler in further comprising a rotatable disc 150 which is mounted to and beneath the insert 134. In this embodiment the disc 150 has the form of a downwardly opening cone. The disc 150 is provided with a spindle 151 which extends upwardly and centrally axially therefrom, which spindle 151 is rotatably received within a tubular member 152 centrally axially mounted within the spirally or helically shaped projections 140 of the tubular section 136. The disc 150 includes an annular downwardly-depending skirt 154, the circumferential outer surface 155 of which includes a plurality of flutes 156. In this embodiment the flutes 156 are axially-aligned. The flutes 156 may, however, be inclined at an angle relative to the axial direction in a similar manner to the flutes 102 provided to the insert 70 as illustrated in FIG. 15. The disc 150 further includes at least one hole 158, preferably a plurality of circularly-extending spaced holes 158, in the region thereof surrounding the rotational axis along which the spindle 151 and the tubular member 152 are located. The holes 158 permit a flow of air from the air chamber 58 into the tubular section 136. In this embodiment, three holes 158 are provided, each of kidney shape, with the holes 158 being slightly spaced from each other in a circular direction so as to define a substantially annular composite air conduit through the disc 150. This inhaler further differs from the above-described known powder inhaler in that, similarly to the inhaler of the above-described third embodiment, the lower tubular part 84 of the first part 48 of the mouthpiece 2 includes a plurality of peripheral holes 104, with the holes 104 being located opposite the circumferential outer surface 155 of the skirt 154. The provision of the holes 104 in the lower tubular part 84 of the first part 48 of the mouthpiece 2 provides additional openings through which supplementary air is drawn when a user inhales by sucking on the mouthpiece 2.

In use, when a user inhales by sucking on the mouthpiece 2, air is drawn not only through the inhalation channel 24 (illustrated in phantom in FIG. 20) but also inwardly through the peripheral holes 104, where the supplementary air drawn through the holes 104 is directed against the flutes 156 on the circumferential outer surface 155 of the skirt 154. This incoming supplementary air tends to impart a rotational force on the disc 150 so as to rotate the same, thereby reducing the possibility of powder accumulating on surfaces, particularly the undersurface 162, of the insert 134. In this embodiment, the supplementary air, after impacting on the flutes 156, passes downwardly into the air chamber 58, through the at least one hole 158 in the disc 150 and thereafter through the tubular section 136 and out of the outlet nozzle 4 of the mouthpiece 2.

FIG. 24 illustrates a first modification of the disc 150 of the inhaler of the above-described sixth embodiment. In this modification the undersurface 162 of the disc 150 is provided with a relief profiling 166 in the form of an array of small recesses 168. By way of example, in the same manner as the recesses 94 provided to the undersurface 86 of the insert 70 as illustrated in FIGS. 9 and 10, the recesses 168 can be any of part-spherical, typically hemi-spherical, or frusto-spherical, the latter consisting of a part-spherical innermost portion inwardly of a frusto-conical portion. Similarly, the array of recesses 168 can have the same packing as the recesses 94 as illustrated in FIG. 10.

FIG. 25 illustrates a second modification of the disc 150 of the inhaler of the above-described sixth embodiment. In this modification the undersurface 162 of the disc 150 is provided with a relief profiling 166 in the form of an array of small projections 170. Again, by way of example, the projections 170 can be any of part-spherical, typically hemi-spherical, or frusto-spherical, the latter consisting of a frusto-spherical innermost portion inwardly of a part-spherical portion. The array of projections 170 preferably has the same packing as the recesses 94 as illustrated in FIG. 10.

In both of the above-described modifications, similarly to the projections 94 and the recesses 96 provided to the undersurface 86 of the insert 70 as illustrated in FIGS. 9 to 11, the provision of the recesses 168 and the projections 170 on the undersurface 162 of the disc 150 assists in preventing the accumulation of powder which impacts thereagainst as a result of the stream of air containing powder being sucked upwardly through the inhalation channel 24.

Figure 26:
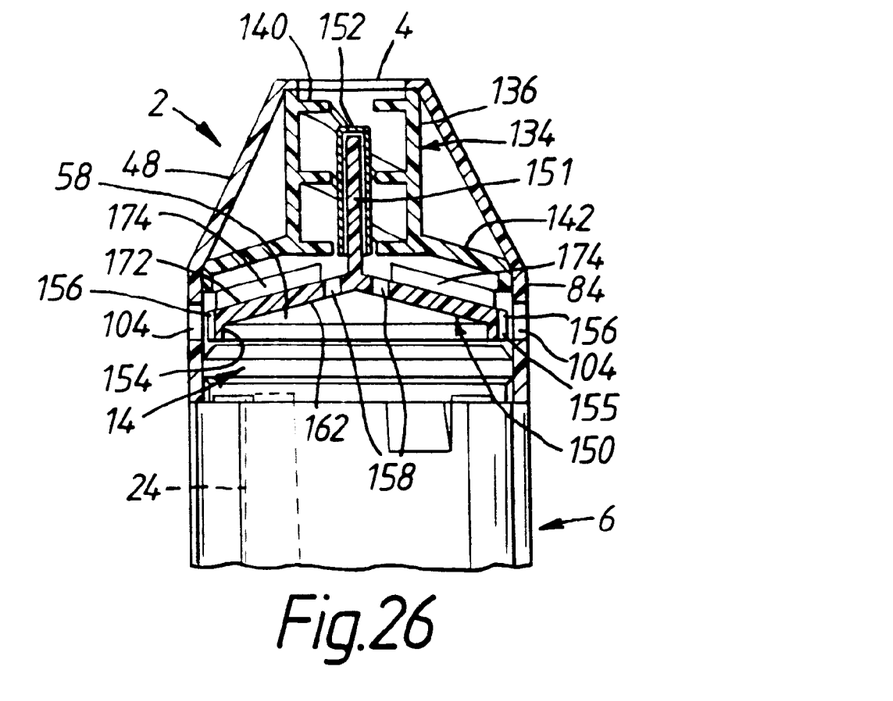
FIG. 26 illustrates a fragmentary part-sectional side view of a powder inhaler in accordance with a seventh embodiment of the present invention.
Figure 27:
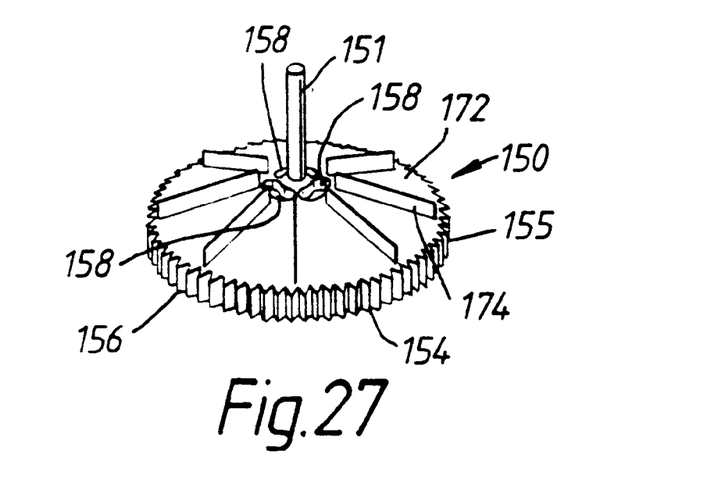
FIG. 27 illustrates a perspective view of the rotatable disc of the inhaler of FIG. 26.

FIGS. 26 and 27 illustrate a powder inhaler in accordance with a seventh embodiment of the present invention.

This inhaler is a modification of the inhaler of the above-described sixth embodiment. Similarly to the inhaler of the above-described sixth embodiment, the first part 48 and the insert 134 of the mouthpiece 2 are fixed to one another. Again, similarly to the inhaler of the above-described sixth embodiment, the insert 134 comprises a tubular section 136 which includes one or more spirally or helically shaped projections 140 that act to deflect the air drawn therethrough and thereby deagglomerate any larger particles of entrained powder, and a substantially radially-directed flange 142, which provides a surface that together with upper surface of the divider 14 defines the air chamber 58. Likewise, similarly to the inhaler of the above-described sixth embodiment, this inhaler comprises a rotatable disc 150 which is mounted to and beneath the insert 134. The disc 150 of this embodiment differs from that of the inhaler of the above-described sixth embodiment only in that the upper surface 172 thereof is provided with a plurality of spaced radially-oriented and upwardly-extending fins 174 which are configured to act as vanes. Similarly to the inhaler of the above-described sixth embodiment, the lower tubular part 84 of the first part 48 of the mouthpiece 2 includes a plurality of peripheral holes 104, with the holes 104 being located opposite the circumferential outer surface 155 of the skirt 154. Differently to the inhaler of the above-described sixth embodiment, however, the peripheral holes 104 extend axially above the circumferential outer surface 155 of the skirt 154. The provision of the holes 104 in the lower tubular part 84 of the first part 48 of the mouthpiece 2 provides additional openings through which supplementary air is drawn when a user inhales by sucking on the mouthpiece 2.

In use, when a user inhales by sucking on the mouthpiece 2, air is drawn not only through the inhalation channel 24 (illustrated in phantom in FIG. 26) but also inwardly through the peripheral holes 104, where the supplementary air drawn through the holes 104 is directed both against the flutes 156 on the circumferential outer surface 155 of the skirt 154 and the radially-directed fins 174 on the upper surface 172 of the disc 150. This incoming supplementary air which impacts the flutes 156 and the radially-directed fins 174 tends to impart a rotational force on the disc 150 so as to rotate the same, thereby reducing the possibility of powder accumulating on surfaces, particularly the undersurface 162, of the insert 134. In this embodiment, the supplementary air, after impacting on the flutes 156 and the radially-directed fins 174, passes through the tubular section 136 and out of the outlet nozzle 4 of the mouthpiece 2.

Finally, it will be understood by a person skilled in the art that the present invention has been described in its preferred embodiments and can be modified in many different ways without departing from the scope of the invention as defined in the appended claims.

What is claimed is:

1. An inhaler for administering powder by inhalation, comprising:
    a plurality of surfaces defining a flow path through which a stream of air is in use drawn on inhalation by a user, where the flow path includes a mouth piece;
    a dosing mechanism for providing a dose of powder to the flow path for entrainment in the steam of air; and
    a movable member downstream of the dosing mechanism for inhibiting accumulation of powder on a surface of the flow path downstream of the dosing means,
    wherein the flow path includes a chamber having an inlet and an outlet,
    wherein the movable member interrupts the stream of air drawn through the inlet of the chamber and is movable at least partially by the stream of air,
    wherein the movable member is a rotatable member which is rotatable about an axis within the chamber so as, in use, to present a moving surface towards which the stream of air containing powder drawn through the inlet of the chamber is directed;
    wherein the rotatable member comprises a tubular section having disposed therein at least one spirally or helically shaped projection and a radially outwardly-extending flange which defines a surface of the chamber.

2. The inhaler of claim 1, wherein the flow path includes a chamber having an inlet and an outlet.

3. The inhaler of claim 2, wherein the movable member interrupts the stream of air drawn through the inlet of the chamber and is movable at least partially by the stream of air.

4. An inhaler for administering powder by inhalation, comprising:
    a plurality of surfaces defining a flow path through which a stream of air is in use drawn on inhalation by a user, where the flow path includes a mouth piece;
    a dosing mechanism for providing a dose of powder to the flow path for entrainment in the steam of air; and
    a movable member downstream of the dosing mechanism for inhibiting accumulation of powder on a surface of the flow path downstream of the dosing means,
    wherein the flow path includes a chamber having an inlet and an outlet,
    wherein the movable member interrupts the stream of air drawn through the inlet of the chamber and is movable at least partially by the stream of air,
    wherein the movable member is a rotatable member which is rotatable about an axis within the chamber and is disposed opposite the inlet of the chamber so as, in use, to present a moving surface towards which the stream of air containing powder drawn through the inlet of the chamber is directed, said axis being disposed parallel to the flow of air from said inlet to said outlet.

5. The inhaler of claim 4, wherein the rotatable member includes at least one element on which the stream of air drawn through the inlet of the chamber acts to cause rotation of the rotatable member on inhalation by the user.

6. The inhaler of claim 4, wherein the mouthpiece comprises a tubular section having disposed therein at least one spirally or helically shaped projection and a radially outwardly-extending flange which defines a surface of the chamber, and the rotatable member is rotatably mounted adjacent a surface of the flange defining the surface of the chamber.

7. The inhaler of claim 6, wherein a lower surface of the flange defines an upper surface of the chamber.

8. The inhaler of claim 7, wherein the flange is disposed opposite the inlet of the chamber.

9. The inhaler of claim 6, wherein the rotatable member comprises a disc.

10. The inhaler of claim 9, wherein the disc has the form of a downwardly-opening cone.

11. The inhaler of claim 9, wherein the disc includes at least one substantially centrally located hole.

12. The inhaler of claim 9, wherein a circumferential outer surface of the disc is a close sliding fit with a circumferential inner surface of the chamber.

13. The inhaler of claim 12, wherein the disc includes a downwardly-depending peripheral skirt which defines the circumferential outer surface thereof.

14. The inhaler of claim 12, wherein the chamber includes a plurality of holes disposed in spaced relation about the periphery thereof through which supplementary air is in use drawn on inhalation by the user and the disc includes at least one air deflecting member which is adapted so as to be acted upon by the supplementary air drawn through the plurality of holes.

15. The inhaler of claim 14, wherein the at least one air deflecting member comprises a plurality of flutes provided to the circumferential outer surface of the disc and the plurality of holes are disposed in opposed relation to the circumferential outer surface of the disc.

16. The inhaler of claim 15, wherein the flutes are aligned parallel to an axis of rotation of the disc.

17. The inhaler of claim 15, wherein the flutes are inclined to an axis of rotation of the disc.

18. The inhaler of claim 14, wherein the at least one air deflecting member comprises a plurality of fins disposed on a surface of the disc directed away from the inlet of the chamber.

19. The inhaler of claim 18, wherein the fins are substantially radially directed.

20. The inhaler of claim 9, wherein a surface of the disc opposed to the inlet of the chamber includes a relief profiling.

21. The inhaler of claim 20, wherein the relief profiling comprises an array of recesses.

22. The inhaler of claim 20, wherein the relief profiling comprises an array of projections.

23. An inhaler for administering powder by inhalation, comprising:
    a plurality of surface defining a flow path through which a stream of air is in use drawn on inhalation by a user, where the flow path includes a mouth piece;
    a dosing mechanism for providing a dose of powder to the flow path for entrainment in the steam of air; and
    a movable member downstream of the dosing mechanism for inhibiting accumulation of powder on a surface of the low path downstream of the dosing means,
    wherein the flow path includes a chamber having an inlet and an outlet,
    wherein the movable member interrupts the stream of air drawn through the inlet of the chamber and is movable at least partially by the stream of air,
    wherein the movable member is a rotatable member which is rotatable about an axis within the chamber so as, in use, to present a moving surface towards which the stream of air containing powder drawn through the inlet of the chamber is directed, said axis being disposed parallel to the flow of air from said inlet to said outlet, wherein the rotatable member comprises a disc comprising a plurality of angled vanes that are tilted slightly from a plane perpendicular to said axis.

24. The inhaler of claim 23, wherein the angled arms are shaped and configured so as to provide no direct flow path between the inlet and the outlet of the chamber.

25. An inhaler for administering powder by inhalation, comprising:

a plurality of surfaces defining a flow path through which a stream of air is in use drawn on inhalation by a user, where the flow path includes a mouth piece;

a dosing mechanism for providing a dose of powder to the flow path for entrainment in the steam of air; and a movable member downstream of the dosing mechanism for inhibiting accumulation of powder on a surface of the flow path downstream of the dosing means, wherein the flow path includes a chamber having an inlet and an outlet, wherein the movable member interrupts the stream of air drawn through the inlet of the chamber and is movable at least partially by the stream of air, wherein the movable member is a rotatable member which is rotatable about an axis within the chamber and is disposed opposite the inlet of the chamber so as, in use, to present a moving surface towards which the stream of air containing powder drawn through the inlet of the chamber is directed, wherein the rotatable member includes at least one element on which stream of air drawn through the inlet of the chamber acts to cause rotation of the rotatable member on inhalation by the user, wherein the rotatable member comprises a tubular section having disposed therein at least one spirally or helically shaped projection and a radially outwardly-extending flange which defines a surface of the chamber.

26. The inhaler of claim 25, wherein the flange is disposed opposite the inlet of the chamber.

27. The inhaler of claim 26, wherein a surface of the flange opposed to the inlet of the chamber includes a relief profiling.

28. The inhaler of claim 27, wherein the relief profiling comprises an array of recesses.

29. The inhaler of claim 27, wherein the relief profiling comprises an array of projections.

30. The inhaler of claim 25, wherein the mouthpiece comprises a first, outer part which is gripped by the lips of the user and a second, inner part disposed therewithin, the rotatable member comprising the inner part, with a lower surface of the flange defining an upper surface of the chamber.

31. The inhaler of claim 30, wherein a circumferential outer surface of the flange is a close sliding fit with a circumferential inner surface of the outer part of the mouthpiece.

32. The inhaler of claim 31, wherein the flange includes a downwardly-depending peripheral skirt which defines the circumferential outer surface of the flange.

33. The inhaler of claim 30, wherein the outer part of the mouthpiece includes a central spindle about which the inner part of the mouthpiece is rotatably mounted.

34. The inhaler of claim 30, wherein the outer part of the mouthpiece includes an annular sleeve within which the inner part of the mouthpiece is rotatably mounted.

35. The inhaler of claim 30, wherein the outer part of the mouthpiece includes a plurality of holes disposed in spaced relation about the periphery thereof through which supplementary air is drawn on inhalation by the user and the inner part of the mouthpiece includes at least one air deflecting member which is adapted so as to be acted upon by the supplementary air drawn through the plurality of holes.

36. The inhaler of claim 35, wherein the at least one air deflecting member comprises a plurality of flutes provided to the circumferential outer surface of the inner part of the mouthpiece and the plurality of holes in the outer part of the mouthpiece are disposed in opposed relation to the circumferential outer surface of the inner part of the mouthpiece.

37. The inhaler of claim 36, wherein the flutes are aligned parallel to an axis of rotation of the inner part of the mouthpiece.

38. The inhaler of claim 36, wherein the flutes are inclined to an axis of rotation of the inner part of the mouthpiece.

39. The inhaler of claim 35, wherein the at least one air deflecting member comprises a plurality of angled blades surrounding the tubular section of the inner part of the mouthpiece.

* * * * *

UNITED STATES PATENT AND TRADEMARK OFFICE
CERTIFICATE OF CORRECTION

PATENT NO. : 6,257,232 B1
DATED : July 10, 2001
INVENTOR(S) : Jan Anderson et al.

Page 1 of 1

It is certified that error appears in the above-identified patent and that said Letters Patent is hereby corrected as shown below:

Title page,
OTHER DOCUMENTS, should include -- International Search Report --

ABSTRACT,
Line 4, delete ";" after "mouthpiece"

Column 1,
Line 3, after "Inhalation Device" insert -- This is a continuation of International Patent Application No. PCT/SE98/00465, with an international filing date of 13 March 1998, now pending. --

Column 5,
Line 47, insert -- Brief Description of the Drawings --

Column 8,
Line 55, after "is" insert -- similarly to the --

Signed and Sealed this

Fifth Day of February, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,257,232 B1
DATED : July 10, 2001
INVENTOR(S) : Jan Anderson et al.

It is certified that error appears in the above-identified patent and that said Letters Patent is hereby corrected as shown below:

<u>Title page,</u>
Item [73], Assignee, the name should be changed from "Astra Akteibolag" to Astra Aktiebolag --.

Signed and Sealed this

Eighteenth Day of June, 2002

Attest:

JAMES E. ROGAN
Attesting Officer
Director of the United States Patent and Trademark Office